United States Patent [19]

Smith

[11] 4,289,824

[45] Sep. 15, 1981

[54] HIGH FLUID-HOLDING ALLOY RAYON FIBER MASS

[75] Inventor: Frederick R. Smith, Toms Brook, Va.

[73] Assignee: Avtex Fibers Inc., Valley Forge, Pa.

[21] Appl. No.: 82,352

[22] Filed: Oct. 5, 1979

Related U.S. Application Data

[63] Continuation-in-part of Ser. No. 790,129, Apr. 22, 1977, Pat. No. 4,199,367, which is a continuation-in-part of Ser. No. 629,952, Nov. 7, 1975, Pat. No. 4,136,697, and Ser. No. 696,451, Jun. 11, 1976, abandoned.

[51] Int. Cl.³ .................... D02G 3/00; D04H 1/58
[52] U.S. Cl. ................... 428/288; 128/156; 128/284; 128/285; 428/361; 428/362; 428/393; 428/394; 428/395
[58] Field of Search ............... 428/393, 392, 364, 373, 428/361, 375, 224, 288; 128/285, 284, 156

[56] References Cited

U.S. PATENT DOCUMENTS

| | | | |
|---|---|---|---|
| 2,901,813 | 9/1959 | Schappel | 28/82 |
| 3,005,456 | 10/1961 | Graham | 128/290 R |
| 3,187,747 | 6/1965 | Burgeni et al. | 106/165 |
| 3,318,990 | 5/1967 | Kajitani | 106/164 |
| 3,418,405 | 12/1968 | Kajitani | 264/191 |
| 3,423,167 | 1/1969 | Kuzmak et al. | 264/191 |
| 3,678,031 | 7/1972 | Schoggen | 536/98 |
| 3,719,503 | 3/1973 | Podlas | 99/129 |
| 3,723,413 | 3/1973 | Chatterjee et al. | 128/285 |
| 3,732,686 | 5/1973 | Chatterjee | 128/285 |
| 3,872,196 | 3/1975 | Bridgeford | 264/188 |
| 3,919,385 | 11/1975 | Smith | 264/188 |
| 4,035,195 | 7/1977 | Podlas | 106/194 |
| 4,066,584 | 1/1978 | Allen et al. | 260/17.4 CL |
| 4,104,214 | 8/1978 | Meierhoeter | 260/17.4 CL |
| 4,128,692 | 12/1978 | Reid | 428/378 |
| 4,136,697 | 1/1979 | Smith | 128/285 |

*Primary Examiner*—Lorraine T. Kendell
*Attorney, Agent, or Firm*—A. R. Eglington

[57] ABSTRACT

Article of manufacture comprising alloy fibers having high fluid-holding capacity, the alloy fibers being comprised of a matrix of regenerated cellulose having carboxymethylcellulose uniformly dispersed therein, the latter being the sole additive for increasing the fluid holding capacity of the fibers.

7 Claims, No Drawings

HIGH FLUID-HOLDING ALLOY RAYON FIBER MASS

CROSS REFERENCE

This application is a continuation-in-part of my allowed pending United States patent application Ser. No. 790,129, filed Apr. 22, 1977, now U.S. Pat. No. 4,199,367, which in turn is a continuation-in-part of my copending application Ser. No. 629,952 filed Nov. 7, 1975, now U.S. Pat. No. 4,136,697 and Ser. No. 696,451 filed June 11, 1976, and now abandoned, and refiled as Ser. No. 811,793, filed June 30, 1977, now U.S. Pat. No. 4,144,079.

The present invention is directed to alloy fibers having high fluid-holding capacity, to shaped articles comprising such fibers and a method of preparing them.

Known in the art are alloy fibers consisting of a matrix of regenerated cellulose and an additive imparting a fluid-holding capacity to these alloy fibers which is greater than that of conventional regenerated cellulose fibers. This advantage is at least partially offset by their higher manufacturing costs.

As employed throughout the description and claims, the terminology "alloy fibers" refers to cellulose fibers having an additive uniformly dispersed through their regenerated cellulose matrix. Similarly, "fluid-holding capacity" is a measure of liquid absorbed into the fibers of a mass of alloy fibers, together with the liquid retained within the interstices of such fiber mass.

This invention relates to alloy rayon staple fibers containing about 10 to 40% sodium carboxymethylcellulose preferably 15 to 35% based on the weight of cellulose ("b.o.c.") and having high fluid holding capacity at least 5.5 cc per gram (such as in the range of up to about 7 cc/g) as measured by the Syngyna test. In the fiber at least about three fourths of the carboxylic groups of the carboxymethylcellulose are in sodium salt form. The fibers carry a lubricating finish, preferably water-soluble polyoxyethylene sorbitan mono-laurate (e.g., AHCO7596T, ICI Industries) or similar nonionic polyoxyethylene sorbitan monoester of higher fatty acid. The proportion of finish and the proportion of the carboxyl groups which are in sodium salt form are such that when a mass of the fibers is wetted with 2 or more times its dry weight of water and then dried, without tension, in air at 25° C. the resulting fibers are substantially non-adherent. The fiber pH (measured on a 1% slurry of these lubricated fibers in deionized water) is in the range of about 5.5 to 8.5 preferably about 6 to 8. Generally the fibers are of about 1½ to 6 denier and the staple fiber length is in the range of about ¾ to 5 inches (such as about 1½ inches).

The fibers may be produced by a process which includes the steps of adding carboxymethylcellulose to viscose, spinning the mixture into fiber form into an acid spin bath, washing to remove adhering acid, desulfurizing and treating the fibers with the lubricating finish, the conditions being such that in the course of this treatment at least about three fourths (such as 80%, 90% or more) of the carboxyl groups of the carboxymethylcellulose are converted to the sodium salt form.

Preferably the process is one which yields "chemically crimped" fibers, the spinning conditions being such that the acidic fibers leaving the acid spin-bath are plastic and stretchable (e.g., stretchable by some 60% or more of their length) are are then stretched, as in a hot aqueous bath, to a considerable degree (e.g., some 60% or more such as about 60–70%), after which the stretched acidic fibers are cut to staple length and allowed to relax (e.g., in hot water) and to crimp; then the wet staple fibers are washed, desulfurized and lubricated as described above, in a process including a step of supplying sufficient alkali so as to convert at least three fourths of said carboxyl groups to the sodium form.

The fibers may be cut and immediately subjected to the relaxation in hot water at a stage when the regeneration of the cellulose xanthate (to cellulose) has not been fully completed, such as when the degree of regeneration (of the fibers being cut) is less than about 95% but above about 85%, such as about 90 to 95%, or after complete regeneration. The relaxation may take place in a conventional bath of hot water (into which chips of parallel fibers, formed by cutting of the tow, fall directly from the cutter); this water may be acidic, neutral or alkaline, e.g. made alkaline with NaOH to a pH of 8 to 11, such as about 10 to 11. A desirable crimp level is at least about 8 distinct crimps per inch (such as about 8 to 20). Discussions of chemical crimping of non-alloy rayon fibers are found, for instance, in Merion et al. U.S. Pat. No. 2,517,694; Textile Research Journal Vol., 23 pp. 137–157 and Man-Made Fibres by Moncrief (6th Edition, 1975, publ. by John Wiley & Sons) pp. 191–193.

The degree and type of fiber lubrication and the degree of conversion of carboxyl groups to sodium carboxylate groups are such that the wet lubricated fibers have considerable resistance to compaction and tend to separate from each other after they have been squeezed together (to express excess water) under pressure and then released. Thus when the fibers are dried they show little tendency to adhere to neighboring fibers, and the product (particularly after conventional rayon "opening") is made up substantially entirely of individual non-bonded fibers.

The Syngyna test involves the following procedure: the fibers are carded into web form and then separated into 2.5 gram portions each about 6 inches long. Each sub web portion is then individually rolled in the direction of its width to provide a six inch roll and a string is looped about the center thereof. Each such roll is then folded on itself at the string loop and drawn into a ½ inch diameter (1.27 cm.) tube within which it is compressed by a clamp and plunger, thus forming a tampon. The resulting tampons are removed, and allowed to stand for a period of about 30 minutes (during which the tampons recover to a bulk density of about 0.4 g/cc). They are then evaluated for their capacity to hold water by the Syngna Method, as described G. W. Rapp in a June 1958 publication of the Department of Research, Loyola University, Chicago, Ill.

The alloy fibers of the present invention are adapted for use in a variety of articles, such as surgical dressings, pads and vaginal tampons, in which high fluid retention is an essential characteristic. In the manufacture of such articles, the alloy fibers may be used in the same manner and with the same equipment as employed with conventional rayon fibers. They may be blended with other fibers which may or may not enhance the absorbent properties of the resulting articles.

Fibers with which the alloy fibers of the present invention may be blended include, for example, rayon, cotton, chemically modified rayon or cotton, cellulose acetate, nylon, polyester, acrylic, polyolefin, etc. Typically a tampon is an elongated cylindrical mass of compressed fibers, which may be supplied within a tube which serves as an applicator; see U.S. Pat. Nos. 2,024,218; 2,587,717; 3,005,456; 3,051,177. The fiber of this invention has been converted into yarns and woven into fabrics having textile application.

The spin bath is an acid bath containing sulfuric acid and sodium sulfate and usually, zinc sulfate. Other coagulation modifiers, as desired, may be present. It is preferred that the $H_2SO_4$ concentration be on the relatively low side, such as 6.0 or 6.8% or (with appropriate other conditions) in a range of about 5.5–8%. During the spinning of the viscose into the acid bath, hydrogen ions diffuse into the stream of viscose emerging from each spinneret hole. The reaction of the acid with caustic soda in the viscose produces sodium slufate and water; the acid also decomposes xanthate groups. The presence of sodium sulfate in the spin bath acts to induce coagulation of the viscose streams owing to dehydration from the interiors of the streams. Zinc ions in the spin bath act, at least at the surfaces of the streams, to convert sodium cellulose xanthate of the viscose to zinc cellulose xanthate which is decomposed more slowly by the acid and thereby keeps the fiber in more stretchable and orientable condition.

Typically the temperature of the acid bath is in the range of about 45° to 65° C. (such as about 50°–55° C.) and the fiber, after passing through the acid bath, is subjected to a bath of water (or dilute acid) first at a high temperature such as about 80° C. to the boiling point, e.g. about 85°–95° C. and/or to steam and then to water at a moderate temperature such as about 40° to 50° C. In the high temperature aqueous treatment the fibers are subjected to stretching. While for most uses the fibers need not have high strength properties, the alloy fibers have been found to retain to a very large extent the physical properties of non-alloy rayon. Typically, the alloy fibers of this invention are not brittle and may be processed in about the same ways as ordinary rayon.

While the polyoxyethylene sorbitan monoester of a higher fatty acid (such as the AHCO series) is a preferred finish, it is within the broader scope of the invention to employ other lubricating finishes, preferably applied in aqueous solution or dispersion, such as soaps; sulfonated oils; ethoxylated fatty acids; ethoxylated fatty ester of polyhydric alcohols; fatty acid esters combined with emulsifying agents or mixtures of various lubricating finishes. Generally, the amount of lubricating finish deposited on the fiber will be well below 1%, and usually more than 0.05%, such as in the range of about 0.1 to 0.5% or 0.1 to 0.3%. Preferably it is not such as to give the fibers an oily feel.

The following Examples illustrate the invention.

EXAMPLE 1

Using conventional rayon spinning equipment, an aqueous alkaline solution of sodium carboxymethylcellulose of 7 M grade (Hercules) having an average degree of substitution of 0.7 carboxymethyl units per anhydroglucose unit of the cellulose, and having a molecular weight such that the viscosity of a 2% solution thereof in water is about 300 cps, is injected by a metering pump into a viscose stream during its passage through a blender and the blend is thereafter extruded. During this, the blend is subjected to high mechanical shearing. The viscose composition is 9.0% cellulose, 6.0% sodium hydroxide and 31% (based upon the weight of the cellulose) carbon disulfide. The viscose ball fall is 60 and its common salt test is 7. In making the alkaline CMC feed solution, the sodium carboxymethylcellulose (CMC) is added to a 6% aqueous solution of NaOH to form a uniform solution having a ball fall viscosity of 120 seconds (which is a viscosity of about 13,000 cps). The addition amount of CMC is such as to provide 20% thereof based on the weight of cellulose in the spinning solution.

The mixture of viscose and sodium carboxymethylcellulose is extruded through a spinneret (having 980 circular holes, each 0.0035 inch in diameter—0.0089 cm.) into an aqueous spinning bath consisting of 6.0% by weight of sulfuric acid, 21% by weight of sodium sulfate, and 1.0% by weight of zinc sufate at 55° C.

The two formed in the spin bath is passed around a driven roll and then pulled (by a second driven roll) through a hot aqueous stretch bath (e.g. containing about 3 to 5% $H_2SO_4$ and at about 85° C. or higher). The exit speed (i.e., the speed at the surface of the second driven roll) is 40 meters/minute, and the speed ratio of the first and second driven rolls is such that the tow is stretched about 60 to 70% in the stretch bath.

The length of travel of the tow in the spin bath is about 0.4 meter and in the stretch bath about 2 meters. After leaving the second driven roll, the tow drops into a cutter and the resulting cut fibers drop into flowing hot water (about 85° to 90° C.) where relaxation and crimping occurs. The 3 denier per filament (d.p.f.) staple fibers are taken up as a blanket, washed with hot water for 8 minutes at 90° C.; treated for 8 minutes in a 0.5% NaOH solution at 40° C. (or equivalent solution of sodium carbonate or sodium sulfide) to neutralize the adhering acid; washed again in water for 4 minutes at 40° C.; bleached and desulfurized in an aqueous solution of sodium hypochlorite containing about 0.2% available chlorine and about 0.2% NaOH at 40° C. for 3 minutes; washed with soft water for 8 minutes at 40° C. (if the pH of the final dried product indicates the presence of free alkali (e.g. NaOH) in the fiber, the process may be modified to include addition of dilute $H_2SO_4$ to the wash water in amount sufficient to neutralize the free alkali).

To the fibers there is then applied an aqueous solution of 0.3% AHCO7596T, after which the fibers are squeezed to remove adhering water and then dried (e.g. at about 90° C.) without tension. In squeezing to remove water, the blanket (about 2 to 4 inches thick—5.08 to 10.16 cm) of the staple fibers is passed between stainless steel pressure rolls, the blanket being in the nip of this pair of rolls for less than 2 seconds and the pressure being such that the average water content of the blanket is reduced thereby to less than about 100% (e.g. about 80%). The blanket is then passed over a beater having a rotating spiked roll which tears it into chunks (e.g. of 1 to 2 inch diameter—2.54 to 5.08 cm. or more) of fiber before drying, e.g. in hot air at 70° or 90° C.

At a level of CMC additions of twenty percent, b.o.c., the fluid holding capacity was 6.8 cc/g in the Syngyna test.

EXAMPLE II

A viscose solution is prepared to contain 9% cellulose, 6% NaOH and 31% $CS_2$ based on cellulose content, and aged, for spinning, to a ball-fall viscosity of 44 seconds and salt index of 5.8.

A solution of sodium carboxymethylcellulose (CMC7L, Hercules, Inc.) is prepared to contain 9% CMC dissolved in 6% NaOH.

The CMC solution is mixed with the viscose solution, just before spinning, by use of a metering pump. The mixed solutions are pumped through a 980 hole jet at a rate to make 3 denier filaments, the jet being immersed in a spin bath containing 6% $H_2SO_4$, 0.78% $ZnSO_4$ and 21.3% $Na_2SO_4$ at 54° C. After travelling 20 inches through the spin bath the yarn bundle is passed around a guide, a godet wheel, through a cascade trough and around a pair of wash drums. The cascade trough cntains an aqueous 2 to 3% $H_2SO_4$ solution at 90° C. The wash drums have a peripheral speed sufficiently higher than that of the godet wheel that the yarn is stretched about 76%. The yarn is washed with water until free of spin-bath chemicals.

Portions of the yarn are cut about 1½ inches long; (3.81 cm treated with sufficient ½% NaOH to convert all the carboxyl groups to sodium form, washed with water and immersed in a 0.3% AHCO 759, solution. Excess solutions are removed by centrifuging. The samples are dried and evaluated for fluid holding capacity using the Syngyna test.

The same process is carried out with a control and with different proportions of CMC injected into the viscose solution, with the following results in terms of fluid holding capacity; using the Syngyna method.

| Sample | % CMC b.o.c* | Fluid held cc/g |
|---|---|---|
| A | 0 | 4.32 |
| B | 10 | 4.94 |
| C | 20 | 5.86 |
| D | 30 | 6.63 |

*% Sodium carboxymethylcellulose, based on cellulose; calculated by dividing the weight of the sodium carboxymethylcellulose added to the viscose solution by the weight of the cellulose in that viscose solution (prior to the addition of CMC).

EXAMPLE III

A viscose solution, similar to that used in Example II, was used with a solution of carboxymethylcellulose (Hercules 4M6SF) in which 540 g of CMC 4M6SF were dispersed in 1000 ml of isopropanol and then mixed with a solution of 2000 g of 18% sodium hydroxide and 2675 ml of water. The solution thus prepared was mixed in various proportions with viscose and spun. The spun fibers were treated as in the previous examples to convert CMC in the fiber to a salt form. AHCO 7596T was the finish employed here. Portions of the fiber were then evaluated for fluid holding capacity, using the Syngyna test. The results were as follows:

| Sample | % CMC 4M6SF b.o.c. | Fluid Held cc/g |
|---|---|---|
| A | 0 | 3.6 |
| B | 10 | 5.7 |
| C | 20 | 6.2 |
| D | 30 | 7.3 |
| E | 40 | 7.7 |

The invention has been illustrated more particularly in connection with sodium carboxymethylcellulose having a degree of substitution in the range of about 0.6 to 1 such as Hercules 7M (having about 0.65-0.85 carboxymethyl groups per anhydroglucose unit, and a degree of polymerization "D.P." of about 1000); or Hercules 7L (also having about 0.65-0.85 carboxymethyl groups per anhydroglucose unit, but whose D.P. is about 400); or Hercules 4M (having about 0.38-0.55 carboxymethyl groups per anhydroglucose unit and a D.P. of about 1000). It is also within the broader scope of the invention to employ CMC of higher degrees of substitution such as about 0.9 or even 1.2 or 1.4, and CMC of higher or lower molecular weight (e.g. a D.P. of about 3200 or about 200, or even 100).

It is known in the art (U.S. Pat. No. b 3,005,456 to Graham) that carboxymethylcellulose (CMC), in fibrous form, and of a low degree of substitution, (i.e., not more than 0.35 carboxyalkyl radicals per glucose residue in cellulose), is substantially insoluble in water, may increase the fluid absorbency of pads or tampons prepared therefrom.

The present invention provides a means of using CMC of higher degree of substitution (DS) than 0.35, including DS of 0.4 to 1.2, to make fibers which have, in the form of pads or tampons, higher fluid absorbency. The fibers of the present invention are a mixed polymer composition, wherein cellulose is the major component and CMC is the minor component. These fibers are insoluble in water, and even though the CMC component is soluble in water, most of it is prevented from going into solution by being trapped in the cellulose matrix.

I claim:

1. An article of manufacture comprising a highly fluid absorbent mass of alloy rayon staple fibers consisting essentially of a matrix of regenerated cellulose and about 10 to about 40 percent of sodium carboxymethylcellulose b.o.c., at least about three-fourths of the carboxyl groups of said carboxymethylcellulose being in sodium salt form, said fibers having a denier of about one and one-half to six; said fibers carrying a lubricating or protective finish in an amount of less than one percent, and said fibers having a fluid holding capacity of at least about 5.5 cc. per gram of fiber as measured by the Syngyna test.

2. The article of claim 1 wherein said sodium salt is present in the regenerated cellulose in an amount ranging from about 15 l to 35 weight percent based on the weight of the cellulose.

3. The article of claim 1 wherein the fibers have a lubricating finish for cellulose thereon.

4. The article of claim 1 in the form of surgical dressing.

5. The article of claim 1 in the form of a tampon.

6. An article as in claim 1 wherein said lubricating or protective finish comprises a nonionic polyoxyethylene sorbitan monoester of a higher fatty acid.

7. An article as in claim 1 wherein said fibers are staple fibers, said article comprising a non-woven array of said staple fibers.

* * * * *

UNITED STATES PATENT AND TRADEMARK OFFICE
CERTIFICATE OF CORRECTION

PATENT NO. : 4,289,824

DATED : September 15, 1981

INVENTOR(S) : Frederick R. Smith

It is certified that error appears in the above-identified patent and that said Letters Patent are hereby corrected as shown below:

Column 6, line 48, that portion of the range reading "15 1" should read --- 15 ---.

Signed and Sealed this

Tenth Day of November 1981

[SEAL]

Attest:

GERALD J. MOSSINGHOFF

Attesting Officer

Commissioner of Patents and Trademarks